United States Patent

Stover et al.

[11] Patent Number: 6,122,047
[45] Date of Patent: Sep. 19, 2000

[54] METHODS AND APPARATUS FOR IDENTIFYING THE MATERIAL OF A PARTICLE OCCURRING ON THE SURFACE OF A SUBSTRATE

[75] Inventors: John C. Stover, Charlotte, N.C.; Songping Gao, Southborough, Mass.; Michael E. Fossey, Woodland Hills, Calif.; Lee Dante Clementi, Lake Wylie, S.C.

[73] Assignee: ADE Optical Systems Corporation, Charlotte, N.C.

[21] Appl. No.: 09/231,685

[22] Filed: Jan. 14, 1999

[51] Int. Cl.[7] .................................................. G01N 21/88
[52] U.S. Cl. .................................... 356/237.3; 356/327.4; 356/338
[58] Field of Search .............................. 356/231.1, 237.2, 356/237.3, 237.4, 237.5, 371, 343, 446, 338; 250/559.41

[56] References Cited

U.S. PATENT DOCUMENTS

| | | |
|---|---|---|
| 3,653,767 | 4/1972 | Liskowitz . |
| 4,893,932 | 1/1990 | Knollenberg . |
| 5,037,202 | 8/1991 | Batchelder et al. . |
| 5,046,847 | 9/1991 | Nakata et al. . |
| 5,363,187 | 11/1996 | Hagiwara et al. .................... 356/237.3 |
| 5,436,464 | 7/1995 | Hayano et al. . |
| 5,471,298 | 11/1995 | Moriya . |
| 5,515,163 | 5/1996 | Kuperschmidt et al. . |
| 5,712,701 | 1/1998 | Clementi et al. ..................... 356/237.2 |
| 5,883,710 | 3/1999 | Nikoonahad et al. ................ 356/237.2 |
| 5,903,342 | 5/1999 | Yatsugake et al. .................. 356/237.5 |

*Primary Examiner*—Hoa Q. Pham
*Attorney, Agent, or Firm*—Alston & Bird LLP

[57] ABSTRACT

The composition of a particle occurring on the surface of a smooth substrate is identified by impinging the surface with a light beam having a strong P-polarized component at an oblique angle of incidence to the surface, and collecting light scattered from the surface at forward, center, and back locations relative to the portion of the surface impinged by the incident beam. The intensities of the light collected at these locations are measured by detectors and converted into signals, and the magnitudes of the signals are compared to correlations of particle material as a function of the relative magnitudes of the forward-, center-, and back-scatter signals so as to identify the material whose correlation most nearly matches the measured detector signals. Preferably, a ratio of the back detector signal magnitude to forward detector signal magnitude is correlated with particle material and back detector signal magnitude. Alternatively or additionally, a ratio of back detector signal magnitude to center detector signal magnitude is correlated with particle material and back detector signal magnitude. Average particle diameter versus back detector signal magnitude is correlated with particle material.

32 Claims, 3 Drawing Sheets

METHODS AND APPARATUS FOR IDENTIFYING THE MATERIAL OF A PARTICLE OCCURRING ON THE SURFACE OF A SUBSTRATE

FIELD OF THE INVENTION

The invention relates to optical inspection of the smooth surface of a substrate such as a silicon wafer, computer disk, computer flat display screen, or the like.

BACKGROUND OF THE INVENTION

Optical inspection methods are frequently used for inspecting the quality of a smooth surface of a substrate such as a silicon wafer, computer disk, or the like. In most such inspection systems, the surface is impinged with a beam of laser light and the light scattered and reflected from the surface is collected and converted into electrical signals that are analyzed so as to infer the presence and size of certain defects on the surface. At least in the case of optical inspection of silicon wafers that are used as the starting material for making integrated circuit chips, a type of defect of major concern is contamination of the surface by particles.

Particles on the wafer surface can interfere with the lithography process by which lines of electrically conductive material are formed on the surface. As a general rule, any particle whose diameter is larger than half the width of the electrical lines to be laid onto the surface constitutes an unacceptable defect. If there are too many such particles, the wafer must be rejected. Currently, integrated circuits are being made with line widths as small as 0.25 $\mu$m (250 nm), so that particles larger than 125 nm in diameter occurring on the wafer surface would be cause for rejecting the wafer, while particles smaller than 125 nm would be tolerable. The semiconductor industry is quickly moving towards production of circuits composed of 0.18 $\mu$m and then 0.15 $\mu$m lines, which means that much smaller particles will soon cause concern.

Wafer inspection systems must be calibrated in order to function properly to accurately determine the diameter of a particle. The calibration is typically done by intentionally placing a plurality of particles of various known diameters on the wafer surface and inspecting the wafer with the inspection apparatus, so that the scattered light intensities produced from the various sizes of particles can be correlated to the particle sizes. These calibration particles are usually spheres made of polystyrene latex (PSL).

One difficulty that has been encountered in wafer inspection processes is that identically sized particles of different material types can produce substantially different scattered light intensities. Stated differently, two particles made of different materials and having substantially different diameters may produce virtually the same measured scattered light intensity. For example, it has been found that silicon particles of a given diameter will produce a much larger scatter intensity than the same diameter PSL particle. In fact, among the various types of materials that can commonly appear on a wafer surface in the form of particles, PSL particles tend to be one of the lowest sources of light scattering. Thus, after the inspection apparatus has been calibrated with PSL particles, the apparatus will tend to overestimate the diameters of silicon particles and those of many other materials. Accordingly, wafers are rejected as having particles larger than half the line width, even though in reality the particles may be smaller than half the line width. Therefore, the accuracy with which particles can be sized by light scattering can be greatly increased if something is known about the particle material.

Another advantage to the semiconductor industry in being able to identify particle material is that this information provides a strong clue as to the source of the contamination. Because particle contamination has to be reduced to a level where useful product can be produced, finding and eliminating contamination sources quickly is economically important.

For light of a given wavelength, every material has an index of refraction n, which indicates how much the speed of light is reduced within the material, and an absorption coefficient k, which is generally indicative of how opaque the material is to the light. The combination of n and k, which are known as the material constants, is unique for each different material. The combinations of n and k can be roughly separated into four groups: (1) dielectrics such as PSL, $SiO_2$, and $Al_2O_3$ (low n and k=0); (2) semiconductors such as silicon (large n and small k); (3) gray metals such as tungsten (large n and large k); and (4) good conductors such as silver (small n and large k).

The combination of particle material, along with particle shape and the n and k values of the substrate surface (which are known), completely and uniquely define the pattern of light scattered by the particle for any given light source. Moreover, for particles whose average diameter is less than about one-fifth of a wavelength of the illuminating light, the particle shape does not play a significant role in determining the scatter pattern. Thus, for visible light and particles smaller than about 100 nm, knowledge of the average particle diameter and the various material constants are enough to calculate the scatter pattern for a given scattering geometry. This fact has allowed the development of scattering models that predict scatter patterns for a given set of conditions. These models have been experimentally confirmed and the results published.

What would be desirable is a system and method for solving the more difficult inverse problem. That is, it would be desirable to be able to determine the particle material and average particle diameter from a knowledge of the scatter pattern. Heretofore, methods have been developed for determining average particle diameter by analyzing the scatter pattern, for example as described in commonly owned U.S. Pat. No. 5,712,701, which is hereby incorporated herein by reference. However, as noted above, the accuracy of such methods depends on the calibration of the system, and currently the calibration must be performed using PSL spheres, which have substantially different material constants from some of the other materials that can appear as particles on a wafer.

Methods for identifying particle material have been proposed. For instance, U.S. Pat. No. 5,037,202 to Batchelder et al. discloses methods and apparatus in which two parallel light beams that are initially mutually coherent but of different polarizations are focused onto a focal plane (such as the surface of a wafer) such that they are displaced apart from each other at the focal plane. After the beams are reflected from the surface, a further optical system intercepts the beams and combines them so that a particle-induced phase shift in one of the beams is manifest by a change in the elliptical polarization of the combined beams. A first detector is responsive to the combined beam's intensity along a first polarization axis to produce a first output, and a second detector is responsive to the combined beam's intensity along a second polarization axis to produce a second output. The first and second outputs are added to provide an extinction signal and are subtracted to provide a phase shift signal. The phase shift and extinction are correlated with index of refraction of the particle material, and hence the identity of the material purportedly can be determined based on the phase shift and extinction values. The size of the particle purportedly can be inferred from its position on a curve of extinction versus phase shift. Thus, in Batchelder's system and method, information about the particle is inferred by analyzing the specularly reflected beams. A disadvantage of this approach is that the reflected light is relatively insensitive to changes in particle properties, such that small particles (e.g., particles on the order of 100 nm or smaller) will produce quite small changes in the specularly reflected beams that can be difficult to accurately measure. Accordingly, the Batchelder approach may not be optimum for identifying small particles of the size that begin to cause problems in integrated circuit manufacturing.

U.S. Pat. No. 5,515,163 to Kupershmidt et al. discloses methods and apparatus in which a polarized laser beam is intensity modulated at a first frequency and is split into two orthogonally polarized beams, and the two beams are phase shifted relative to each other at a second frequency. The two phase-shifted beams are directed onto the surface being inspected, and light scattered by particles at an angle to the two beams is detected. The detected light is synchronously demodulated to determine the amplitude of the scattered light at the frequency of intensity modulation and the amplitude and phase of the scattered light at the frequency of phase modulation. These quantities purportedly can be correlated to size and refraction index of particles to permit identification of particles. Kupershmidt's method involves complicated calculations, and the measurements require sampling over a number of modulation cycles in order to obtain accurate measurements for a given scanned portion of the surface being inspected. Accordingly, scanning of the entire surface would likely be relatively slow.

SUMMARY OF THE INVENTION

The inventors have discovered that the more difficult inverse problem of determining particle material and size from a knowledge of the scatter pattern can be solved if the appropriate light source and incident angle of the illuminating beam are used, and if the scatter pattern is measured in enough detail with the appropriate collector geometry.

In accordance with the present invention, the surface of the substrate is impinged by a beam of P-polarized light at an oblique angle of incidence, and scattered light is collected at a plurality of locations spaced apart about the hemispherical space above the surface, including at least a forward location and a back location relative to the illuminated portion of the substrate surface. The intensities of the scattered light at the forward and back locations are measured and converted into signals that define a scatter pattern produce by the particle. The particle material is determined by comparing the detected forward- and back-scatter signal magnitudes with a plurality of predetermined scatter patterns defined by magnitudes of the forward- and back-scatter signals for a plurality of materials. The predetermined scatter pattern that most closely matches the detected scatter pattern is identified, and the material to which the predetermined scatter pattern corresponds is identified as the material of the particle. Advantageously, the substrate is moved relative to the incident beam so as to scan the incident beam over the surface for detecting and identifying particles occurring anywhere on the surface. A significant advantage of the present invention is its ability to quickly identify particle materials based on a single scan of the surface by the incident beam.

Preferably, a wide-angle collector is used to collect light forward-scattered over an area spaced from but proximate the reflected beam. The forward-scattered light advantageously is collected over an area about 20°–50° wide and spaced from the reflected beam by at least about 5°. Still more preferably, the forward-scattered light is collected over an annular area surrounding the reflected beam and having an inner periphery at least about 10° in diameter and an outer periphery about 20° to 50° in diameter. However, other collector geometries and locations can be used for the forward collector if desired, including locations displaced from the incident plane or locations spaced on one side of the reflected beam toward the surface normal that passes through the illuminated portion of the surface.

The back-scattered light preferably is collected over an area about 20°–45° wide. The back-scattered light advantageously can be collected over a generally circular area centered about 45°–75° away from a surface normal passing through the region of the surface illuminated by the incident beam. If desired, the back-scattered light can be collected over an area displaced from an incident plane formed by the incident beam and the surface normal, as shown in FIG. 2.

In accordance with a preferred embodiment of the invention, a first material-discriminating parameter is calculated as a ratio of the magnitude of the back-scatter signal to the magnitude of the forward-scatter signal. Determining the particle material comprises comparing the back/forward ratio and the magnitude of the back-scatter signal to a plurality of correlations of back/forward ratio versus back-scatter signal magnitude for a plurality of materials, and identifying the material whose correlation is closest to a point defined by the measured back/forward ratio and back-scatter signal magnitude. The correlations preferably are stored in a data storage unit, and a comparator preferably is provided for comparing the measured data to the correlations stored in the data storage unit.

In a further preferred embodiment of the invention, once the particle material is determined, an average diameter of the particle is determined from the magnitude of the back-scatter signal based on a correlation between particle material, diameter, and back-scatter signal magnitude. A plurality of correlations of particle diameter with back-scatter signal magnitude corresponding to a plurality of materials advantageously are stored in the data storage unit and the comparator is operable to retrieve the correlation corresponding to the material identified and to determine particle diameter from the back-scatter signal magnitude based on the retrieved correlation.

For certain particle materials and diameters, the correlations based on the back/forward ratio can sometimes converge for two or more materials such that the particle material cannot be reliably identified from a knowledge of the back-scatter signal magnitude and the back/forward ratio. Accordingly, in accordance with another preferred embodiment of the invention, scattered light is collected from a center region of the space proximate a surface normal passing through the illuminated region of the surface, and the intensity of the collected light is measured and converted into a center-scatter signal having a magnitude indicative of said intensity. A second material-discriminating parameter is calculated as a ratio of the magnitude of the back-scatter signal to the magnitude of the center-scatter signal. The particle material is determined based on both the correlation of particle material with the magnitudes of the back-scatter signal and the back/forward ratio and a second correlation of particle material with the magnitudes of the back-scatter signal and the back/center ratio. More particularly, where the correlations based on back/forward ratio do not provide good discrimination of materials, the particle material is determined by comparing the back/center ratio and the magnitude of the back-scatter signal to a second set of correlations of back/center ratio versus back-scatter signal magnitude for a plurality of materials, and identifying the material whose correlation is closest to a point defined by the measured back/center ratio and back-scatter signal magnitude. The second correlation tends to provide adequate discrimination in regions in which the first correlation based on back-to-forward signal ratio does not provide good discrimination. Thus, the overall discrimination capability of the method is improved.

BRIEF DESCRIPTION OF THE DRAWINGS

The above and other objects, features, and advantages of the invention will become more apparent from the following description of certain preferred embodiments thereof, when taken in conjunction with the accompanying drawings in which.

DETAILED DESCRIPTION OF THE DRAWINGS

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
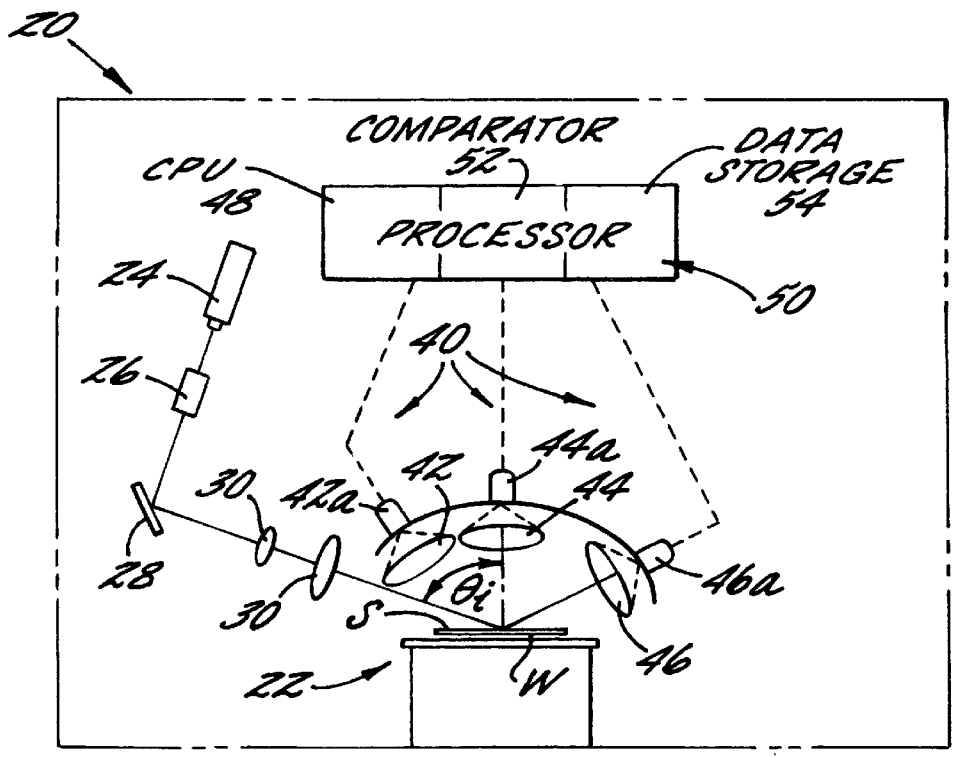
FIG. 1 is a schematic side elevation of an apparatus in accordance with a preferred embodiment of the invention.
Figure 2:
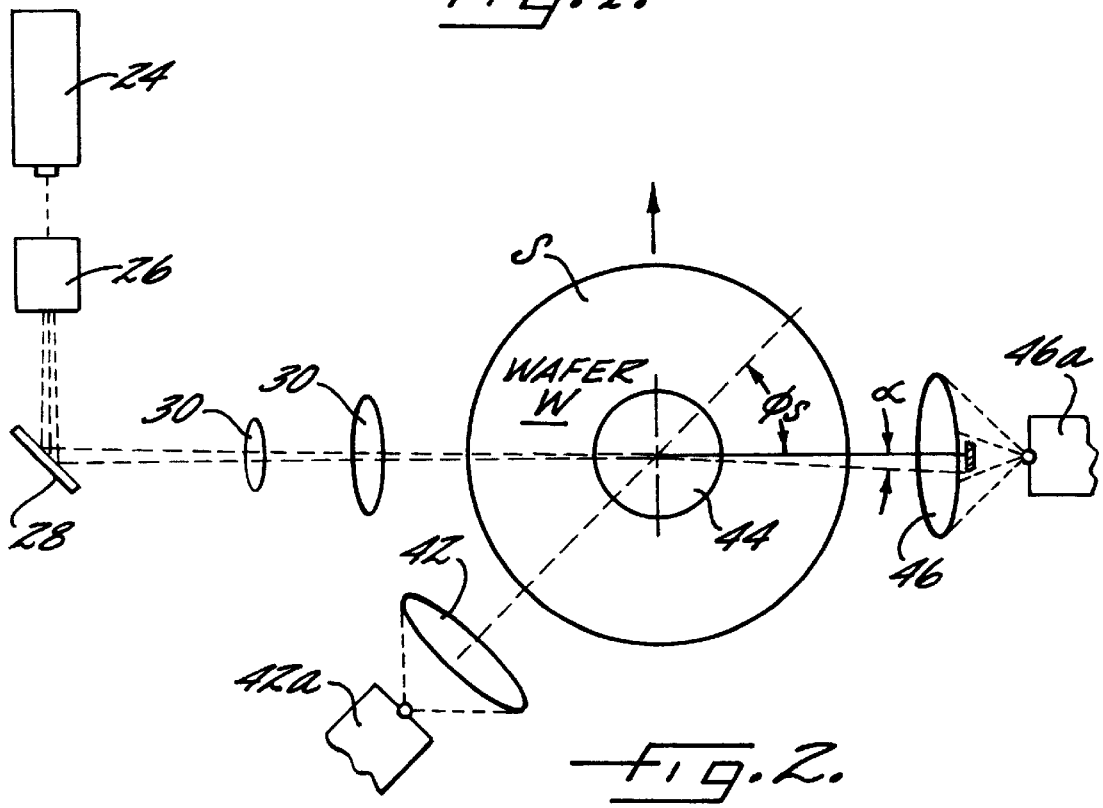
FIG. 2 is a schematic top plan view of the apparatus of FIG. 1.

With reference to FIGS. 1 and 2, an apparatus 20 in accordance with a preferred embodiment of the invention is shown. The apparatus 20 includes a wafer transport device 22 adapted to support a substrate or wafer W to be inspected. For purposes of the present description, it is assumed that the wafer W is supported such that the surface S to be inspected is horizontal; however, it will be understood that the wafer need not be oriented horizontally. The apparatus 20 includes a light source 24 operable for creating a narrow beam of light having a strong P-polarized component. The light source 24 preferably is a laser emitting a light beam in the visible spectrum. Shorter wavelengths tend to produce larger particle scatter signals and thus contribute toward improved accuracy of measurement, while longer wavelengths tend to increase the maximum particle diameter for which the material can be identified and thus extend the particle-diameter range over which the method and apparatus are effective. The emitted beam can be passed through a beam expander 26 if desired, and then the beam is directed with the aid of one or more mirrors such as the mirror 28 and/or one or more lenses such as the lenses 30 such that the beam is impinged on the surface S of the wafer at an oblique angle of incidence $\theta_i$ measured from a surface normal that passes through the region of the surface S illuminated by the incident beam. Preferably, the incident angle $\theta_i$ is fairly large, for example about 45° to 80°, in order to emphasize the differences in scatter intensities for different locations in the hemispherical space above the surface S, as further described below.

Figure 3:
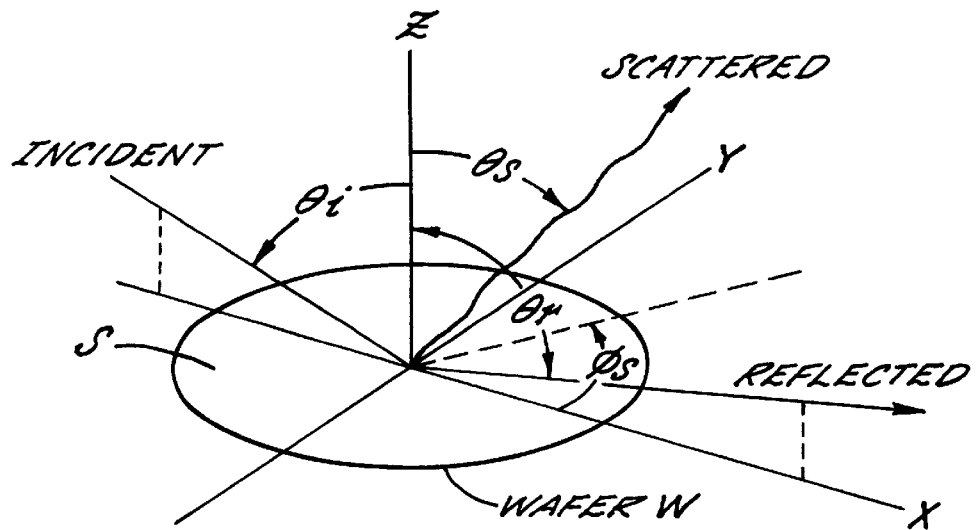
FIG. 3 is a schematic perspective view showing a substrate being impinged by an incident light beam and the light being reflected and scattered from the surface.

As schematically depicted in FIG. 3, the incident beam strikes the surface S at the incident angle $\theta_i$ and is specularly reflected therefrom at a reflected angle $\theta_r$ and is scattered in many directions by imperfections on the surface. A plane of incidence is defined by the incident beam and the surface normal shown as the z-axis. When the incident beam strikes a particle on the surface, the scattered light is scattered out of the plane of incidence as illustrated by the scattered ray $\theta_s$. The polar angle that the scattered ray makes with the plane of incidence is defined as $\phi_s$.

In accordance with the present invention, the scattered light is collected by a plurality of collectors and analyzed in order to determine the material of which a particle detected on the surface S is made. Theoretical calculations were performed with a scattering model in order to predict scattering patterns for a number of different particle sizes and materials. The scattering model employed is based on the discrete sources method, and has been experimentally verified as described in the published literature.

Figure 4:
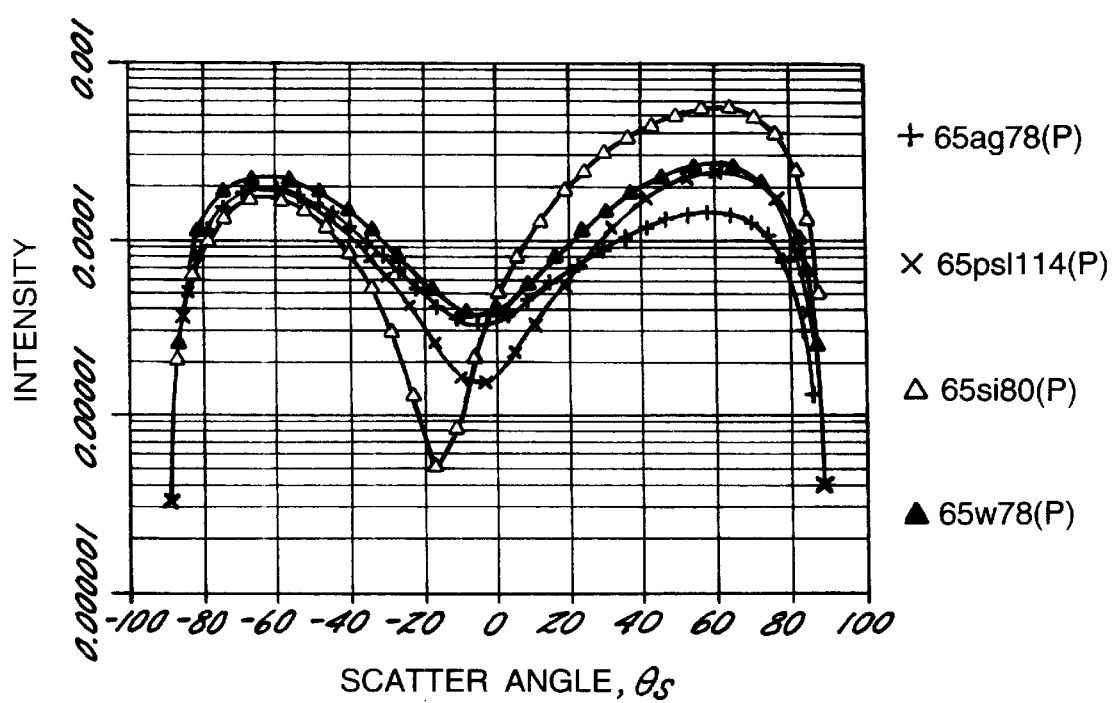
FIG. 4 is a graph showing theoretically calculated intensity of scattered light versus angular position for four particles of different diameters and materials on a silicon substrate when the particles are illuminated by a P-polarized light beam at an oblique angle of incidence.

FIG. 4 shows results of theoretical calculations performed by the scattering model for four different particles (one each from the dielectric, semiconductor, gray metal, and good conductor groups previously described) disposed on a silicon substrate and impinged by an incident beam of P-polarized light having a wavelength of 488 nm at an incident angle of 65 degrees. The optical constants of the four different materials are shown in the following table, along with the diameters of the particles corresponding to FIG. 4:

| Material | Symbol | n | k | Diameter |
|---|---|---|---|---|
| PSL | PSL | 1.59 | 0.0 | 114 nm |
| Silicon | Si | 4.37 | 0.08 | 80 nm |
| Tungsten | W | 3.36 | 2.66 | 78 nm |
| Silver | Ag | 0.25 | 3.14 | 78 nm |

The particle diameters were chosen such that the scattered light intensity in a back region of space above the substrate surface (i.e., at a scatter angle $\theta_s$ less than about −45°) is essentially the same for all four particles. It is clearly seen that the intensities of scattered light in a forward region of the space (i.e., at positive scatter angles greater than about 20°) are substantially different for the different particles. For example, the intensity of light scattered by the silicon particle is substantially larger than the intensity of light scattered by the PSL particle, even though the silicon particle is considerably smaller. Accordingly, if a particle sizing system were based on scattered light intensity in the back region and were calibrated using PSL particles, the diameters of particles of silicon would be seriously overestimated.

In accordance with the present invention, the material of which the particle is made is determined such that the material effects on light scattering intensity are automatically taken into account and a more accurate estimation of particle size can be made. To this end, and with reference to FIGS. 1 and 2, a plurality of scattered light collectors 40 are located in various positions with respect to the illuminated region of the substrate surface. A back collector 42 is located in a back region of the space above the surface S for collecting light scattered in a backward direction (i.e., toward negative scatter angles $\theta_s$). As shown in FIG. 2, the back collector 42 can be displaced from the plane of incidence at a polar angle $\phi_s$ if desired. A center collector 44 is located in a center region of the space above the surface S proximate the surface normal. A forward collector 46 is located in a forward region of the space proximate the specularly reflected beam. The collectors 42, 44, 46 are formed by lenses and/or mirrors that collect scattered light and focus the collected light onto a corresponding detector 42a, 44a, 46a each of which produces a signal indicative of the intensity of the scattered light collected and focused onto the detector.

Each of the collectors 42, 44, 46 extends over a range of scatter angles $\theta_s$ and preferably is generally circular, although other collector shapes can be used. The lenses or mirrors of the collectors effectively integrate the collected scattered light such that the magnitudes of the signals produced by the corresponding detectors represent integrations of the light scattered over the areas of the collectors.

It will be noted in FIG. 4 that there is a large dip in each of the intensity distributions near the surface normal location, such that a pair of "shoulders" are defined in the intensity distribution in forward and back locations relative to the surface normal. It will also be noted that the extent and location of the dip and the magnitude and locations of the shoulders are different for the various particles. The present invention takes advantage of this shifting of the scatter intensity distribution in order to identify particle materials. The dip in the intensity distribution tends to be created when a P-polarized light source is used, as in FIG. 4, or when the light source has a strong P-polarized component. A light source dominated by S-polarization would likely tend to create a smaller dip in the intensity distribution, or perhaps no dip at all, and hence may not work as well, although in some applications it may produce acceptable results.

Figure 5:
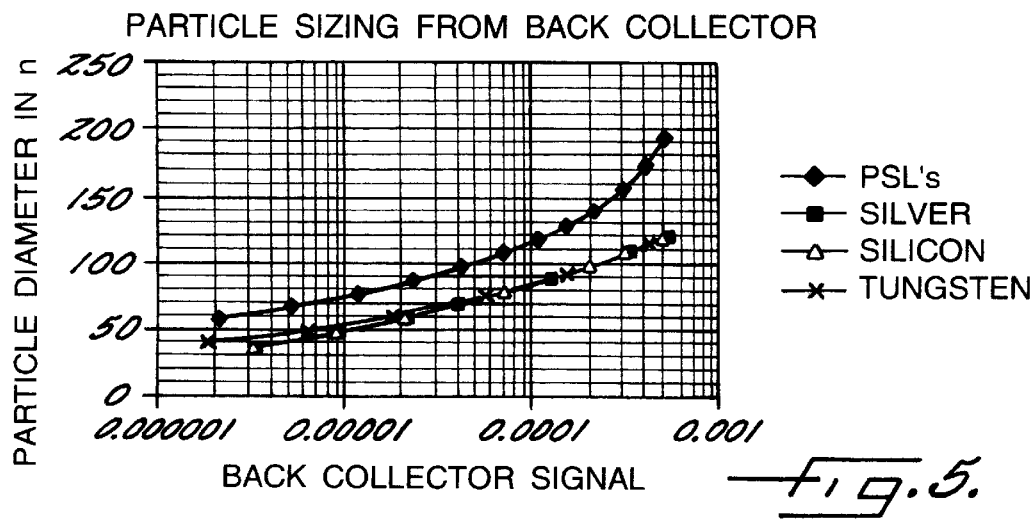
FIG. 5 is a graph showing theoretically calculated results plotted as average particle diameter versus the magnitude of scattered light intensity at the back collector location for the four materials shown in FIG. 4.

In FIG. 4, the scattered light intensities are shown only in the incident plane, but in reality light is scattered over the entire reflective hemisphere. The theoretical model can be run so that the scattered light received over an area corresponding to the area of each of the collectors 42, 44, 46 is integrated to give the total collector signal for the back, center, and forward collectors. FIG. 5 shows the total integrated back collector signal over a range of different particle diameters for the particle materials of FIG. 4. Thus, FIG. 5 can be used to determine particle diameter from the back collector signal if the material is known. It will be noted that the three non-PSL materials are tightly grouped compared to the PSL response. The PSL material is similar in index values to dielectrics sometimes found on wafers, such as $SiO_2$ and $Al_2O_3$. Accordingly, the tight grouping of the non-PSL materials implies that substantial improvements in particle sizing can be made if the low index dielectrics can be separated from the non-dielectric materials.

Figure 6:
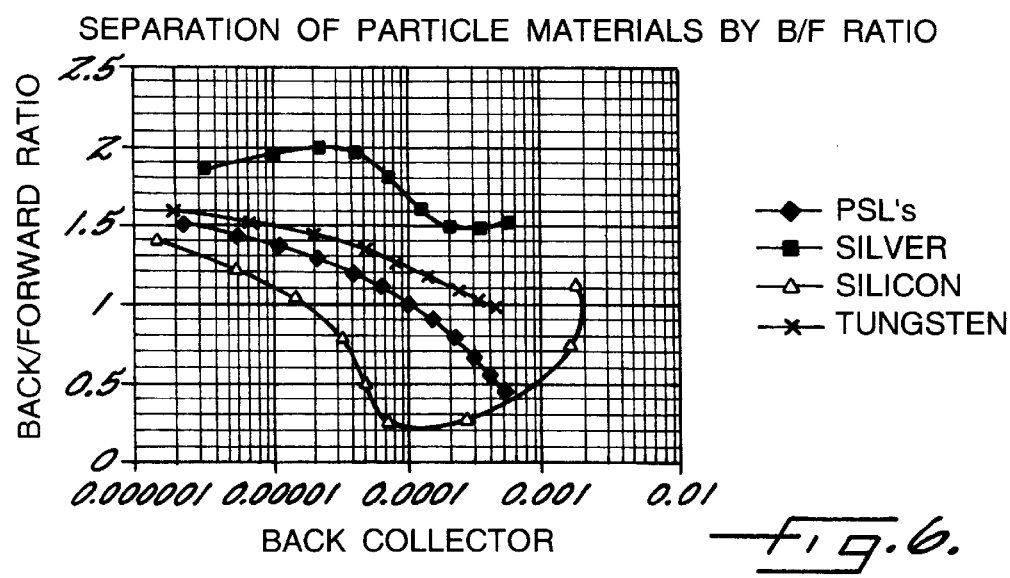
FIG. 6 is a graph showing theoretically calculated results plotted as a ratio of back-to-forward detector signal magnitude versus back detector signal magnitude for the four materials shown in FIGS. 4 and 5.

In FIG. 6, the model results for the same particles as FIG. 5 are plotted in the form of a ratio of the back collector signal magnitude to the forward collector signal magnitude (hereafter the "back/forward ratio") versus the back collector signal magnitude. It can be seen that the curves for the various materials are clearly distinct from one another at least over major ranges of the back collector signal magnitude.

Thus, the back/forward ratio comprises a material-discriminating parameter that can enable the material of a particle to be identified. Based on these results, the following method can be used to determine particle size and material.

The surface S of the substrate is impinged by an incident beam and the collectors 42, 44, 46 collect light scattered by any particle present on the illuminated region of the surface and focus the collected light onto the detectors 42a, 44a, 46a, which produce signals indicative of the intensity of the scattered light. The back/forward ratio is calculated, such as by a CPU 48 of a processor 50 connected to the detectors. The back/forward ratio and back collector signal magnitude are compared, such as by a comparator 52 of the processor 50, to the correlations of particle material with back/forward ratio and back collector signal magnitude shown in FIG. 6. The correlations of particle material with back/forward ratio and back collector signal magnitude advantageously are stored in a data storage unit 54 of the processor 50 such that they can be accessed by the comparator 52. The measured back collector signal magnitude and calculated back/forward ratio define a point on the graph of FIG. 6, and if the scatter is from one of the four materials the point will be close to one of the curves. This determines the particle material. The size of the particle is then determined by using the curve of FIG. 5 that corresponds to the identified material to determine the particle diameter from the back collector signal magnitude.

The apparatus 20 preferably includes a scanning system for relatively moving the wafer W and the incident beam so that the incident beam is scanned across the surface S for detecting and identifying particles occurring anywhere on the surface. The scanning system can include a transport device 22 that translationally and/or rotationally moves the wafer W, and additionally can include a beam-scanning system including rotating mirrors (not shown) for linearly scanning the incident beam across the wafer surface.

Once the particle material is known, the back collector signal magnitude provides a generally reliable indication of particle diameter in most cases. However, it will be appreciated that particle diameter can be inferred based on scattered light intensity measured at other locations, since scattered light intensity generally increases with increasing particle diameter at most locations around the hemisphere. For example, the forward collector signal magnitude can be used instead of the back collector signal magnitude. The forward collector signal magnitude can be particularly useful at least with the specific collector geometry of FIG. 1 for sizing particles larger than about 100 nm in diameter. However, where the forward collector 46 is positioned near the specularly reflected beam, care must be taken in the design of the forward collector such that the specularly reflected beam and light scattering caused by surface roughness effects of the surface S are not detected by the detector. Light scattered by surface roughness tends to closely surround the specularly reflected beam. Accordingly, as shown in FIG. 2, the collector 46 advantageously is annular in shape such that a small circular region including and surrounding the specularly reflected beam is not collected or is blocked from reaching the detector 46a. The half angle α of this undetected region advantageously is at least about 5°; in other words, the inner periphery of the annular collection area of the forward collector 46 preferably has a diameter at least about 10° wide with the specularly reflected beam passing through the center of the undetected circular region. However, it will be appreciated that other collector geometries and locations can be used for the forward collector. For instance, a generally circular forward collector can be positioned symmetrically straddling the incident plane and spaced on one side of the specularly reflected beam between the surface normal and the reflected beam.

The forward collector 46 advantageously has a generally circular outer periphery that is about 20° to 50° wide in diameter. Each of the center collector 44 and back collector 42 advantageously is generally circular and has a diameter about 20° to 45° wide.

Figure 7:
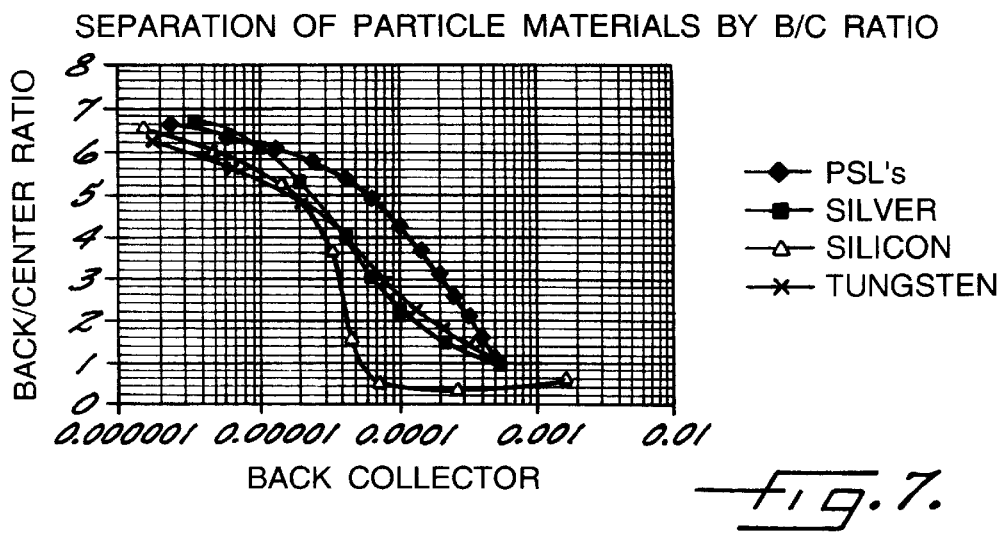
FIG. 7 is a graph showing theoretically calculated results plotted as a ratio of back-to-center detector signal magnitude versus back detector signal magnitude for the four materials shown in FIGS. 4–6.

It will be noted that there are some potential difficulties in FIG. 6. The PSL and tungsten lines are close together at the small particle end, and the silicon line is looping back to cross over the other lines. Any overlapping points, or locations where the lines are too close together, represent locations where materials will not be reliably identified. This situation is improved by introducing a second material-discriminating parameter based on the signal from the center collector 44. More particularly, FIG. 7 shows model-calculated results for the four particle materials of FIG. 6, in which a ratio of back collector signal magnitude to center collector signal magnitude ("the back/center ratio") is plotted against back collector signal magnitude. There are still cross-over points, but PSL and tungsten particles are farther apart at the low-diameter end and silicon is improved at the high-diameter end. Accordingly, the overall material discrimination capability of the method can be improved by using both the first material-discriminating parameter based on the back- and forward-collector signal magnitudes, and the second material-discriminating parameter based on the back- and center-collector signal magnitudes.

Many modifications and other embodiments of the invention will come to mind to one skilled in the art to which this invention pertains having the benefit of the teachings presented in the foregoing descriptions and the associated drawings. For example, the invention has been explained in connection with inspection of silicon wafers, but the methods and apparatus of the invention are equally suitable for inspecting various other non-silicon substrates including computer disks, flat displays, and others. Further, while the method of the invention advantageously is carried out by calculating ratios of the back-to-forward and back-to-center collector signal magnitudes, it will be appreciated that the method of the invention can alternatively be performed by using other material-discriminating parameters, such as the inverse of the described ratios, differences between the collector signals (normalized, if desired, by one of the signals), and other parameters. Moreover, it is possible to identify particle material without explicitly calculating any material-discriminating parameter. For instance, predetermined correlations of particle material with the signal magnitudes of the various collectors can be stored in the data storage device 54 as multi-dimensional arrays that can be accessed by the comparator 52 and interpolated upon or otherwise manipulated in order to identify the particle material that has a stored scatter pattern most nearly matching the measured scatter pattern. Additionally, while preferred geometries for the collectors have been described, other types and geometries of collectors can be used for detecting the scatter pattern produced by a particle. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for inspecting a surface of a substrate to identify the material of which a particle on the surface is made, comprising:

directing an incident beam of light onto a portion of the surface at an oblique angle of incidence such that any particle present on the portion of the surface scatters light in a plurality of directions into a hemispherical space above the surface;

collecting light scattered into each of a plurality of regions of the space;

measuring an intensity of the collected light for each region so as to create a set of scatter data representing a sample of a scatter pattern produced by the particle; and determining the particle material by comparing the measured scatter data with a plurality of predetermined scatter patterns corresponding to a plurality of materials and identifying the material whose scatter pattern most nearly matches the measured scatter data.

2. The method of claim 1, wherein an incident beam of light having a strong P-polarized component is impinged on the portion of the surface.

3. The method of claim 2, wherein the measuring step comprises using a forward detector to measure an intensity of light collected in the forward region of the space so as to produce a forward-scatter signal having a magnitude indicative of said intensity, and using a back detector to measure an intensity of light collected in the back region of the space so as to produce a back-scatter signal having a magnitude indicative of said intensity;

and wherein the step of determining the particle material comprises comparing the magnitudes of the forward- and back-scatter signals to predetermined scatter patterns defined by magnitudes of the forward- and back-scatter signals so as to identify the material whose scatter pattern most nearly matches measured signals.

4. The method of claim 3, further comprising the steps of:

calculating a first material-discriminating parameter by dividing a numerator that is a function of the magnitude of the back-scatter signal by a denominator that is a function of the magnitude of the forward-scatter signal; and determining the particle material based on a correlation of particle material with the magnitude the first material-discriminating parameter and the magnitude of one of the back-scatter signal and the forward scatter signal.

5. The method of claim 4, wherein the step of calculating a first material-discriminating parameter comprises calculating a back/forward ratio by dividing the magnitude of the back-scatter signal by the magnitude of the forward-scatter signal.

6. The method of claim 5, wherein the step of determining the particle material comprises comparing the back/forward ratio and the magnitude of the back-scatter signal to a plurality of scatter patterns defined by back/forward ratio versus back-scatter signal magnitude for a plurality of materials, and identifying the material whose scatter pattern is closest to the measured back/forward ratio and back-scatter signal magnitude.

7. The method of claim 3, further comprising the steps of:
collecting light scattered into a center region of the space proximate a surface normal passing through the illuminated region of the surface and using a center detector to measure an intensity of the collected light so as to produce a center-scatter signal having a magnitude indicative of said intensity; and
comparing the magnitudes of the forward-, center-, and back-scatter signals to predetermined scatter patterns defined by magnitudes of the forward-, center-, and back-scatter signals so as to identify the material whose scatter pattern most nearly matches the measured signals.

8. The method of claim 7, further comprising the steps of:
calculating a first material-discriminating parameter by dividing a numerator that is a function of the magnitude of one of the forward and back detector signals by a denominator that is a function of the magnitude of the other of the forward and back detector signals;
calculating a second material-discriminating parameter by dividing a numerator that is a function of the magnitude of one of the center and back detector signals by a denominator that is a function of the magnitude of the other of the center and back detector signals; and
determining the particle material based on a first correlation of particle material with the magnitudes of the back-scatter signal and the first material-discriminating parameter and a second correlation of particle material with the magnitudes of the back-scatter signal and the second material-discriminating parameter.

9. The method of claim 8, wherein the step of calculating the second material-discriminating parameter comprises calculating a back/center ratio by dividing the magnitude of the back-scatter signal by the magnitude of the center-scatter signal.

10. The method of claim 9, wherein the step of determining the particle material comprises comparing the back/center ratio and the magnitude of the back-scatter signal to a plurality of correlations of back/center ratio versus back-scatter signal magnitude for a plurality of materials, and identifying the material whose correlation is closest to a point defined by the measured back/center ratio and back-scatter signal magnitude.

11. The method of claim 3, wherein the step of collecting the forward-scattered light comprises using a wide-angle collector to collect light scattered over an area spaced from but proximate the reflected beam.

12. The method of claim 3, wherein the step of collecting the forward-scattered light comprises collecting the light over an area having a generally circular outer periphery with a diameter about 20°–50° wide.

13. The method of claim 3, wherein the step of collecting the forward-scattered light comprises collecting the light over an annular area surrounding the reflected beam.

14. The method of claim 3, wherein the step of collecting the back-scattered light comprises collecting the light over an area about 20°–45° wide.

15. The method of claim 3, wherein the step of collecting the back-scattered light comprises collecting the light over a generally circular area centered about 45°–75° away from a surface normal passing through the portion of the surface illuminated by the incident beam.

16. The method of claim 3, wherein the step of collecting the back-scattered light comprises collecting the light over an area displaced from an incident plane formed by the incident beam and the surface normal.

17. The method of claim 3, further comprising the step of determining an average diameter of the particle based on the magnitude of the back-scatter signal and a correlation of particle material with particle diameter and back-scatter signal magnitude.

18. A method for inspecting a surface of a substrate to detect the presence of a particle on the surface and to identify the material of which the particle is made, comprising:
directing an incident beam of light having a strong P-polarized component onto a region of the surface at an incident angle of about 45°–80° from a surface normal passing through the region of the surface such that the incident light is reflected and scattered by the surface;
collecting light scattered from the surface over an area in a forward region of space proximate the beam reflected from the surface, and measuring an intensity of the collected light so as to produce a forward-scatter signal having a magnitude indicative of said intensity;
collecting light scattered from the surface over an area in a center region of the space above the surface proximate the surface normal, and measuring an intensity of the collected light so as to produce a center-scatter signal having a magnitude indicative of said intensity;
collecting light scattered from the surface over an area in a back region of the space above the surface, and measuring an intensity of the collected light so as to produce a back-scatter signal having a magnitude indicative of said intensity; and
determining the particle material based on a correlation of particle material with relative magnitudes of the back-, center-, and forward-scatters signals.

19. The method of claim 18, further comprising the step of calculating a ratio of the magnitude of the back-scatter signal to the magnitude of the forward-scatter signal, and wherein the step of determining the particle material comprises comparing the back/forward ratio and the back-scatter signal magnitude to a plurality of correlations of back/forward ratio versus back-scatter signal magnitude for a plurality of materials, and identifying the material whose correlation is closest to the back/forward ratio and back-scatter signal magnitude.

20. The method of claim 19, further comprising the step of:
calculating a ratio of the magnitude of the back-scatter signal to the magnitude of the center-scatter signal; and
determining the particle material based on both the correlation of particle material with the magnitudes of the back-scatter signal and the back/forward ratio and a correlation of particle material with the magnitudes of the back-scatter signal and the back/center ratio.

21. The method of claim 18, further comprising the step of determining an average diameter of the particle based on the magnitude of the back-scatter signal and a correlation of particle material with particle diameter and back-scatter signal magnitude.

22. A method for inspecting a surface of a substrate to determine the size of a particle on the surface and to identify the material of which the particle is made from a single scan of the surface, comprising:
scanning an incident beam of light having a predominant P-polarized component over a portion of the surface at an oblique angle of incidence such that any particle present on the portion of the surface scatters light into a plurality of spaced-apart regions of a hemispherical space above the surface;

collecting light scattered from a single scan of the incident beam into each of at least two of said regions of the space;

measuring an intensity of the collected light for each region so as to produce a set of scatter data including the magnitudes of the scattered light intensities for each of the regions, the scatter data representing a sampling of a scatter pattern produced by the particle;

determining the size of the particle based on the scatter data; and determining the particle material based on the same scatter data by comparing the scatter data measured for the particle with a plurality of predetermined scatter patterns corresponding to a plurality of materials and identifying the material whose predetermined scatter pattern most nearly matches the measured scatter data.

23. The method of claim 22, wherein the measuring step comprises using a forward detector to measure an intensity of light collected in the forward region of the space so as to produce a forward-scatter signal having a magnitude indicative of said intensity, and using a back detector to measure an intensity of light collected in the back region of the space so as to produce a back-scatter signal having a magnitude indicative of said intensity;

and wherein the step of determining the particle material comprises comparing the magnitudes of the forward- and back-scatter signals to predetermined scatter patterns defined by magnitudes of the forward- and back-scatter signals so as to identify the material whose predetermined scatter pattern most nearly matches the measured signals.

24. The method of claim 23, wherein the step of determining the particle size comprises using the magnitude of one of the forward- and back-scatter signals to determine particle size based on a predetermined correlation corresponding to the material identified in the material-determining step, said predetermined correlation relating particle diameter to the magnitude of said one of the forward- and back-scatter signals.

25. An apparatus for optical identification of the material of a particle on a surface of a substrate, comprising:

a light source operable for creating a beam of light having a strong P-polarized component and for directing the beam onto a portion of the surface at an oblique incident angle such that the light is reflected and scattered from the surface;

a forward collector located above the surface at a location spaced from but proximate the reflected beam, the forward collector being operable to collect forward-scattered light and to focus the collected light;

a forward detector arranged to receive the focused light from the forward collector and operable to produce a signal having a magnitude indicative of the intensity of the forward-scattered light;

a back collector located above the surface and positioned to receive light back-scattered from the surface, the back collector being operable to collect back-scattered light and to focus the collected light;

a back detector arranged to receive the focused light from the back collector and operable to produce a signal having a magnitude indicative of the intensity of the back-scattered light;

a data storage unit that stores a plurality of correlations of particle material with relative magnitudes of the back detector signal and the forward detector signal; and a comparator connected to the storage unit and operable to determine the particle material by comparing the magnitudes of the back detector signal and the forward detector signal with the stored correlations so as to identify the material whose correlation most closely matches the forward and back detector signal magnitude.

26. The apparatus of claim 25, further comprising a data processing unit connected to the forward and back detectors and the comparator, the data processing unit being operable to calculate a first material-discriminating parameter by dividing a numerator that is a function of the magnitude of one of the forward and back detector signals by a denominator that is a function of the magnitude of the other of the forward and back detector signals, the data storage unit storing a first set of correlations of the first material-discriminating parameter versus one of the back and forward detector signal magnitudes for a plurality of materials, and the comparator being operable to determine the particle material by comparing the calculated first material-discriminating parameter and said one of the back and forward detector signal magnitudes with the first set of correlations.

27. The apparatus of claim 25, further comprising:

a center collector positioned for collecting light scattered in a direction generally normal to the surface into a center region of the space above the surface, the center collector being operable to collect center-scattered light and to focus the collected light; and a center detector arranged to receive the focused light from the center collector and operable to produce a signal having a magnitude indicative of the intensity of the center-scattered light;

the data storage unit storing a set of correlations of particle material with back detector signal magnitude and the second material-discriminating parameter corresponding to the plurality of materials;

the comparator being operable to determine the particle material by comparing the magnitudes of the back detector signal and the center detector signal with the correlations.

28. The apparatus of claim 27, further comprising a data processing unit connected to the back, center, and forward detectors and the comparator, the data processing unit being operable to calculate a second material-discriminating parameter by dividing a numerator that is a function of the magnitude of one of the center and back detector signals by a denominator that is a function of the magnitude of the other of the center and back detector signals, the data storage unit storing a second set of correlations of the second material-discriminating parameter versus one of the back and forward detector signal magnitudes for a plurality of materials, and the comparator being operable to determine the particle material by comparing the calculated second material-discriminating parameter and said one of the back and forward detector signal magnitudes with the second set of correlations.

29. The apparatus of claim 27, wherein the center collector is generally circular and has a diameter about 20°–45° wide.

30. The apparatus of claim 25, wherein the forward collector comprises an annular collector configured to collect light over an annular area that surrounds the reflected beam.

31. The apparatus of claim 30, wherein the forward collector has an inner perimeter spaced at least about 5° from the reflected beam and a radial extent of about 10°–25°.

32. The apparatus of claim 25, wherein the back collector is generally circular and has a diameter about 20°–45° wide.

* * * * *